US009561179B2

(12) United States Patent
Castan et al.

(10) Patent No.: US 9,561,179 B2
(45) Date of Patent: Feb. 7, 2017

(54) CONTROLLED-RELEASE FLOATING PHARMACEUTICAL COMPOSITIONS

(75) Inventors: Catherine Castan, Orlienas (FR); Philippe Caisse, St Bonnet de Mure (FR)

(73) Assignee: FLAMEL IRELAND LIMITED, Dublin (IE)

( * ) Notice: Subject to any disclaimer, the term of this patent is extended or adjusted under 35 U.S.C. 154(b) by 279 days.

(21) Appl. No.: 12/790,201

(22) Filed: May 28, 2010

(65) Prior Publication Data

US 2010/0310667 A1    Dec. 9, 2010

Related U.S. Application Data

(60) Provisional application No. 61/182,537, filed on May 29, 2009.

(30) Foreign Application Priority Data

May 29, 2009  (FR) ...................................... 09 53601
May 28, 2010  (WO) ................. PCT/FR2010/051038

(51) Int. Cl.
A61K 9/14    (2006.01)
C08B 3/06    (2006.01)
A61K 9/00    (2006.01)
A61K 9/50    (2006.01)

(52) U.S. Cl.
CPC ........... *A61K 9/0065* (2013.01); *A61K 9/5078* (2013.01)

(58) Field of Classification Search
None
See application file for complete search history.

(56) References Cited

U.S. PATENT DOCUMENTS

| | | | |
|---|---|---|---|
| 3,976,764 A | | 8/1976 | Watanabe et al. |
| 4,101,650 A | | 7/1978 | Umezawa |
| 4,844,905 A | | 7/1989 | Ichikawa et al. |
| 5,626,876 A | * | 5/1997 | M uller et al. ............... 424/484 |
| 6,261,601 B1 | | 7/2001 | Talwar et al. |
| 2004/0208936 A1 | * | 10/2004 | Chorin et al. ................ 424/490 |
| 2007/0275969 A1 | * | 11/2007 | Gurny et al. ............. 514/237.5 |
| 2008/0317841 A1 | * | 12/2008 | Grenier et al. ............... 424/451 |

FOREIGN PATENT DOCUMENTS

| | | |
|---|---|---|
| CN | 101288659 A | 10/2008 |
| EP | 0709087 A1 | 5/1996 |
| EP | 1524968 A2 | 4/2005 |
| EP | 1524969 A2 | 4/2005 |
| FR | 2263744 A1 | 10/1975 |
| WO | WO-99/01112 A1 | 1/1999 |
| WO | WO-01/58424 A1 | 8/2001 |
| WO | WO-02/102415 A1 | 12/2002 |
| WO | WO-03/030878 A2 | 4/2003 |
| WO | WO-2006/063858 A1 | 6/2006 |
| WO | WO-2006/131566 A2 | 12/2006 |
| WO | WO-2007/010400 A2 | 1/2007 |
| WO | WO-2009/138642 A1 | 11/2009 |

OTHER PUBLICATIONS

Bulgarelli et al., "Effect of matrix composition and process conditions on casein-gelatin beads floating properties," International journal of pharmaceutics, 2000; 198(2): 157-165.
Jain et al., "Porous Carrier Based Floating Granular Delivery System of Repaglinide," Drug Development and Industrial Pharmacy, 2007; 33(4): 381-391.
Joseph et al., "A floating-type oral dosage form for piroxicam based on hollow polycarbonate microspheres: in vitro and in vivo evaluation in rabbits," Journal of Controlled Release, 2002; 79(1-3): 71-79.
Rouge et al., "Comparative pharmacokinetic study of a floating multiple-unit capsule, a high-density multiple-unit capsule and an immediate-release tablet containing 25 mg atenolol," Pharm Acta Helv., 1998; 73(2): 81-87.
Streubel et al.,"Floating microparticles based on low density foam powder," International Journal of Pharmaceutics, 2002; 241(2): 279-292.
Bulgarelli et al., "Effect of matrix composition and process conditions on casein-gelatin beads floating properties," International journal of pharmaceutics, 2000; 198(2): 157-165. (abstract).
Choi et al., "Preparation of alginate beads for floating drug delivery system: effects of CO2 gas-forming agents," International Journal of Pharmaceutics, 2002; 239: 81-91.
Jain et al., "Porous Carrier Based Floating Granular Delivery System of Repaglinide," Drug Development and Industrial Pharmacy, 2007; 33(4): 381-391. (abstract).
Joseph et al., "A floating-type oral dosage form for piroxicam based on hollow polycarbonate microspheres: in vitro and in vivo evaluation in rabbits," Journal of Controlled Release, 2002; 79(1-3): 71-79. (abstract).
Rouge et al., "Comparative pharmacokinetic study of a floating multiple-unit capsule, a high-density multiple-unit capsule and an immediate-release tablet containing 25 mg atenolol," Pharm Acta Helv., 1998; 73(2): 81-87. (abstract).
Streubel et al.,"Floating microparticles based on low density foam powder," International Journal of Pharmaceutics, 2002; 241(2): 279-292. (abstract).

(Continued)

Primary Examiner — Melissa Javier
(74) Attorney, Agent, or Firm — Porzio, Bromberg & Newman P.C.

(57) ABSTRACT

The invention relates to a pharmaceutical composition comprising a plurality of controlled-release coated microparticles each comprising a floating core, on the surface of which is deposited a layer containing at least one active principle, said layer being covered with a controlled-release coating, characterized by the fact that said floating core is composed of cellulose acetate phthalate and has an apparent density of less than or equal to 0.6 g/mL and said coated microparticles have a density of less than or equal to 0.7 g/mL.

14 Claims, 10 Drawing Sheets

(56) References Cited

OTHER PUBLICATIONS

Takenaka et al., "Polymorphism of spray-dried microencapsulated sulfamethoxazole with cellulose acetate phthalate and colloidal silica, montmorillonite, or talc," J. of Pharmaceutical Sciences, 1981; 70(11), pp. 1256-1260.

International Search Report for PCT/FR2010/051038, mailed Sep. 16, 2011.

* cited by examiner

CONTROLLED-RELEASE FLOATING PHARMACEUTICAL COMPOSITIONS

FIELD OF THE INVENTION

The present invention relates to floating pharmaceutical compositions or floating multiparticulate systems and their preparation process. The invention also relates to the application of these floating systems for the controlled release of pharmaceutically active principles, in particular those having an absorption window situated in the upper part of the stomach.

STATE OF THE ART

Many studies have been carried out to improve the effectiveness of pharmaceutical compositions, in particular by controlling the release profile of the pharmaceutically active principles that they contain. However, even if the duration of release can be significantly extended or delayed, the period of action of these pharmaceutical preparations, and therefore their effectiveness, is highly dependent on the residence time in the stomach, in particular when the active principle is absorbed only in the upper part of the gastro-intestinal tract. The relatively short duration, the high degree of variability and the unpredictability of the residence time in the stomach are major obstacles in the optimization of the effectiveness of these forms.

Various solutions have been proposed to increase the residence time in the stomach. There can be mentioned for example gastroretentive systems which, in the presence of the gastric juices, dilate sufficiently or expand to reach a size greater than that of the pyloric opening, mucoadhesive systems which adhere to the stomach wall, systems whose high density keeps them in the lower part of the gastric bag. Finally, floating systems can be mentioned, the low density of which keeps them in the upper part of the stomach contents.

Patent application WO 01/58424 (West Pharma) describes a floating particle system comprising a core containing an active principle, then an enteric polymer film-coating, then a layer of chitosan powder deposited by mixing, and a hydrophobic layer constituted by magnesium stearate. The flotation performances are assessed with a test in 500 mL of 0.1 N hydrochloric acid for 30 min, without stirring and in the absence of a surfactant.

Other studies have concerned multiparticulate floating systems. Rouge N. et al. in Pharm. Acta Helv. 73(2) 81-87 (1998) described minitablets based on a swelling hydrophilic polymer (HPMC) of 3 mm diameter incorporated in a gelatin capsule. Others again have prepared microparticles by using various low-density porous supports such as polycarbonate microspheres (Joseph N. J. et al. (Journal of Controlled Released (2002) 79, 71-79), calcium silicate microspheres (Jain Sunil K. et al. (Drug Development and Industrial Pharmacy (2007) 33, p. 381-391), polypropylene particles (Streubel A. et al. (International Journal of Pharmaceutics 198 (2002), 279-292), calcium alginate beads (Choi B. Y. et al. (International Journal of Pharmaceutics 239 (2002) 81-91) or gelatin and casein beads (Bulgarelli E. et al., International Journal of Pharmaceutics 198 (2000), 157-165).

In the patent FR 2263744 (Eisai Co), polystyrene minitablets (6 mm×9 mm) or puffed rice grains are used as floating supports, but the relatively significant volume of these products does not allow the use of a large number of supports per administration. Moreover, these substances are not approved for pharmaceutical use.

The applicants of U.S. Pat. No. 5,626,876 (Muller—Lohmann Therapie Systeme—1997) use porous elements in order to obtain floating pharmaceutical forms. In particular, one of the embodiments describes a plurality of floating subsystems constituted by a foam particle, covered with a layer containing a pharmaceutically active principle, and optionally a second layer of film-coating providing control of the release. These foam particles are based on expanded polymers of the polystyrene, polyamide or polypropylene type, marketed under the trade mark Accurel (Armak Company, Chicago, now Akzo Chemicals). These polymers are not authorized for oral administration and are considered by the manufacturer as microsponges capable of absorbing several times their weight of a liquid which can be water. They are therefore non-floating. In fact, in the presence of a liquid medium, the pores, which are open pores, fill, the density of the material is increased and the particles sink. An active principle can therefore only be deposited by the dry route, unless a waterproofing layer as mentioned in column 2 lines 55-57 is deposited on their surface beforehand. Moreover, no quantitative indication is given for the flotation ability of the various finished products described in the patent.

Floating microspheres constituted by a core containing a pharmaceutically active principle and a polymer matrix, surrounded by an intermediate layer containing at least one insoluble (hydrophobic or fatty) and porous excipient, preferably glycerol behenate or dibasic calcium phosphate, and a film constituted by a polymer allowing the controlled release of the active principle, are described in patent application WO 2006/063858 (US 2008/0317841 Grenier et al.). Again, no quantitative indication of the duration of flotation of these microparticles is given in the patent application.

Another solution for producing floating systems consists of generating gas in situ in order to reduce the density of the tablets or granules (U.S. Pat. No. 4,844,905, U.S. Pat. No. 4,101,650, WO 2007/010400, U.S. Pat. No. 6,261,601). Generally these systems include an alkaline carbonate salt which, on contact with the acid gastric juices, and sometimes as a result of the presence of an acid in the formulation, generates in situ carbon dioxide. The latter is trapped in the gelled hydrophilic matrix which constitutes the pharmaceutical form, based on polymers such as hydroxypropyl methylcellulose, or polysaccharides such as xanthan, caroub, guar gums, or chitosan derivatives. Patent application WO 02/105415 describes effervescent floating monolithic or multiparticulate systems based only on the powder of seeds from the garden cress *Lepidium sativum*. Such effervescent systems are not desirable as it is always very difficult to adjust the level of effervescence accurately, especially in microparticles, and thus to have a constant and reproducible buoyancy between the different particles.

Thus, there is a real need for multiparticulate floating systems which are easy to implement and low-cost and which make it possible in a simple, accurate and reproducible fashion to adapt the release profile to the extended residence time in the stomach.

BRIEF DESCRIPTION OF THE INVENTION

It is to the Applicant's credit to have responded to this need with pharmaceutical compositions comprising a plurality of microparticles each comprising a floating core on which is deposited a layer of active principle covered with a controlled-release coating layer.

The pharmaceutical composition of the invention is multiparticulate, i.e. it is constituted by a large number of microparticles (for example several hundred or even several thousands). This multiplicity statistically ensures a good reproducibility of the transit kinetics of the active principle in the whole of the gastrointestinal tract, resulting in improved control of the bioavailability and therefore an improved effectiveness. As a result of this plurality of microparticles, it is easy to combine microparticles containing different active principles, each capable of release with a different kinetics and independently of the others.

Once administered by the oral route, the composition according to the invention releases coated microparticles (or granules) which remain in the upper part of the gastric contents so that their residence time in the stomach is extended. The coating of the granules is suitable for a controlled release of the active principle, controlled release which takes into account this residence time in the stomach.

The composition according to the invention has advantages compared to systems based on swelling and gelling matrices or those which effervesce in the stomach: on the one hand, the dimensions of the coated particles remain practically constant, allowing a control and reproducibility of the release; on the other hand, flotation is immediate and does not require a period of time for hydration, swelling or effervescent reaction during which the form would not float and would thus risk expulsion through the pylorus.

DETAILED DESCRIPTION OF THE INVENTION

Thus, a subject of the invention is a pharmaceutical composition comprising a plurality of controlled-release coated microparticles each comprising a floating core, on the surface of which is deposited a layer containing at least one active principle, said layer being covered with a controlled-release coating, said floating core having an apparent density of less than or equal to 0.6 g/mL, preferably less than or equal to 0.5 g/mL and even more preferably less than or equal to 0.4 g/mL, and said coated microparticles having an apparent density of less than or equal to 0.7 g/mL, preferably less than or equal to 0.6 g/mL and even more preferably less than or equal to 0.5 g/mL.

A subject of the invention is more particularly a pharmaceutical composition comprising a plurality of controlled-release coated microparticles each comprising a floating core, on the surface of which is deposited a layer containing at least one active principle, said layer being covered with a controlled-release coating, characterized by the fact that said floating core is composed of cellulose acetate phthalate and has an apparent density of less than or equal to 0.6 g/mL and said coated microparticles have an apparent density of less than or equal to 0.7 g/mL.

A subject of the invention is also a pharmaceutical composition comprising a plurality of controlled-release coated microparticles each comprising a floating core, on the surface of which is deposited a layer containing at least one active principle, said layer being covered with a controlled-release coating, characterized by the fact that said floating core is composed of cellulose acetate phthalate.

The floating cores according to the invention advantageously have a closed porosity greater than or equal to 0.2, preferably greater than or equal to 0.4, preferably greater than or equal to 0.6.

The floating cores advantageously have a floatability F as measured according to the flotation test described hereafter in the TESTS section, greater than or equal to 50% after 1 hour, preferably greater than or equal to 50% after 4 hours, more preferably greater than or equal to 50% after 6 hours and even more preferably greater than or equal to 50% after 8 hours.

The different densities are understood according to the definition given in the European Pharmacopoeia, edition 6.4, monograph 02.02.42. More specifically the following definitions are given:

True density ($\rho_v$): this density takes into account only the volume occupied by the solid, excluding intra- or interparticle spaces. This density is measured using a helium pycnometer, the helium gas penetrating the closed pores.

Effective particle density ($\rho_p$): this density takes into account the volume occupied by the solid and the volume of the closed pores of the particles. This is achieved by using a liquid pycnometer according to the test for measuring the effective particle density described below in relation to the TESTS section.

Apparent density ($\rho_a$): the apparent density obtained after settling of the bed of powder according to the test for measuring the apparent density after settling described below in relation to the TESTS section. The volume considered comprises the volume of the particle and the intraparticle volume of the settled bed of powder.

Within the meaning of the invention and in the whole of the present disclosure, the term "active principle" covers not only the active principle as such but also its salts, enantiomers, isomers, solvates or polymorphic forms.

The term "coating" or the term "film-coating" are used interchangeably to denote the layer controlling the release of the active principle.

The coating is called "controlled-release" if it allows the release of the active principle to be modified, delayed or sustained. Such coatings have been widely described in the literature and those which are quite particularly suited to the invention are those described in particular in patent applications EP 0 709 087, WO 03/030878, EP 1 524 968, EP 1 524 969 and PCT/FR2009/050719.

According to the invention, by "floating core composed of cellulose acetate phthalate" is meant a floating core which comprises at least 50% by weight of cellulose acetate phthalate, preferably at least 60% by weight, preferably at least 70% by weight, preferably at least 80% by weight, preferably at least 90% by weight, preferably at least 95% by weight, preferably at least 98% by weight of cellulose acetate phthalate. In a particularly advantageous embodiment, the floating core is essentially constituted by cellulose acetate phthalate.

Floating Cores:

Said floating cores are compatible with an oral administration of the pharmaceutical form.

The floating cores used have an apparent density of less than or equal to 0.6 g/mL, preferably less than or equal to 0.5 g/mL, and even more preferably less than or equal to 0.4 g/mL.

According to a particular embodiment, the floating cores according to the invention have a closed porosity such that the effective particle density is always less than the true density. The closed porosity is calculated as follows:

$$\text{Closed porosity} = 1 - \frac{\rho_p}{\rho_v}$$

According to another particular embodiment, the floating cores according to the invention have a closed porosity greater than or equal to 0.2, preferably greater than or equal to 0.4, preferably greater than or equal to 0.6.

According to another embodiment of the invention, the floating cores are porous.

According to another embodiment of the invention, the floating cores have a floatability F as measured according to the flotation test described hereafter in the TESTS section, greater than or equal to 50% after 1 hour, preferably greater than or equal to 50% after 4 hours, more preferably greater than or equal to 50% after 6 hours and even more preferably greater than or equal to 50% after 8 hours.

The floating cores used in the microparticles of the composition of the invention have substantially no open porosity; they therefore allow the active principle to be deposited directly by the wet route without requiring an intermediate layer.

According to a preferred embodiment, the equivalent volume mean diameter of the floating cores is comprised between 50 µm and 4000 µm. A sieving operation following standard techniques known to a person skilled in the art can allow defined grain-size sections to be selected. More particularly, said floating cores can have an equivalent volume mean diameter comprised within one of the following ranges: 50 to 500 µm, 500 to 1000 µm or 1000 to 4000 µm.

In a particular embodiment, the floating cores have a sufficient mechanical strength to withstand in particular the shear forces, friction and impacts to which they will be subjected during the process for the preparation of the pharmaceutical compositions according to the invention. In particular, according to an advantageous embodiment, the layer of active principle will be deposited by spraying, using standard techniques, in a fluidized bed device equipped with a Wurster tube or a rotary granulator (for example a GPCG1 from Glatt, Germany). Thus, according to an advantageous embodiment, the floating cores have a mechanical strength, as measured by their friability according to a "friability test" defined hereafter in the TESTS section, which is less than 30%, preferably less than 20%, and more preferably less than 10%.

Certain pharmaceutical excipients, as a result of their production process, can have an apparent density of less than or equal to 0.6 g/mL, a floatability in an aqueous medium of at least 50% for at least 1 hour, a friability of less than 30%, a volume mean diameter comprised between 50 µm and 4000 µm, a closed porosity greater than or equal to 0.2 and can be easily sieved.

This is the case in particular for cellulose acetate phthalate (cellacefate) marketed by Eastman Chemical Company under the trade mark Eastman™ C-A-P Cellulose Ester NF® (FDA Drug Master File #8) in the form of granules or powder. It is known to use cellulose acetate phthalate marketed by Eastman Chemical as a coating polymer in pharmaceutical compositions.

It is to the inventors' credit to have found that it was possible to use this polymer marketed in the form of granules or powder, not as a film-forming enteric polymer, but as a floating core in a floating system of the invention.

Thus, according to an advantageous embodiment, in the pharmaceutical composition of the invention, the floating cores are composed of cellulose acetate phthalate, i.e. they comprise at least 50% by weight of cellulose acetate phthalate, preferably at least 60% by weight, preferably at least 70% by weight, preferably at least 80% by weight, preferably at least 90% by weight, preferably at least 95% by weight, preferably at least 98% by weight of cellulose acetate phthalate. In a particularly advantageous embodiment, the floating core according to the invention is constituted by cellulose acetate phthalate, i.e. it contains approximately 100% by weight of cellulose acetate phthalate. For example, the floating cores according to the invention can be granules of cellulose acetate phthalate. These granules of cellulose acetate phthalate are insoluble in media where the pH is less than 5.5; therefore they are insoluble in the gastric medium and are floating systems within the meaning of the present invention. They float by themselves, which makes it possible to deposit an active principle on their surface by the liquid route, and thus to obtain floating systems without the need to deposit an intermediate waterproofing film.

According to a preferred embodiment, said floating cores are cellulose acetate phthalate granules marketed by Eastman Chemical Company under the trade mark Eastman™ C-A-P Cellulose Ester NF (FDA Drug Master File # 8) in the form of powder or in the form of granules.

Advantageously, the microparticles according to the invention do not comprise effervescent excipients.

Active Principle:

Such pharmaceutical compositions are particularly advantageous for active principles having a short absorption window or having a preferential absorption in the stomach. They can also have an advantage for active principles having a local activity in the stomach, such as for the local treatment of gastric hyperacidity and stomach or duodenal ulcers, and more particularly for treatment against the bacterium *Helicobacter pylori*. The increase in the residence time in the stomach provided by the present invention can allow greater effectiveness of these active molecules and thus make it possible to reduce the minimum dose necessary to eradicate these bacteria.

The active principle is arranged on the surface of the floating core, optionally using a binder, thus forming a layer of active principle which will be covered by the controlled-release coating. This binder allows a better adhesion of the active principle to the floating core. Among the various binders known to a person skilled in the art, water-soluble polymers are used according to an advantageous embodiment of this invention, such as polymers of hydroxypropyl cellulose, hydroxypropyl methylcellulose, povidone, polysaccharides, acacia, agar, carob gums and similar. The nature of the binder selected can depend on its chemical compatibility with the active principle. From a quantitative point of view, this binder is used in proportions of 5 to 95%, preferably 5 to 50% and even more preferably 5 to 20% of the active principle layer. The active principle layer can also contain other excipients used as standard by a person skilled in the art. There can be mentioned in particular dispersants, surfactants, preservatives, buffers, protective agents, colorants and mixtures thereof.

Controlled-Release Coating

The controlled-release coating is applied onto the floating cores covered with the layer of active principle by techniques known to a person skilled in the art, for example by the technique of spray coating in a fluidized bed.

Any type of coating conferring a controlled release can be used in the pharmaceutical compositions of the invention. In particular, there can be mentioned the coatings described in particular in patent applications EP 0,709,087, WO 03/030878, EP 1,524,968, EP 1,524,969 and PCT/FR2009/050719 which are included by way of reference. A person skilled in the art is capable of adjusting the nature of the coating and the film-coating ratio in order to obtain the desired dissolution profile.

Thus, according to a variant of the invention, the controlled-release coating comprises:
at least one water-insoluble film-forming polymer P1,
at least one water-soluble polymer P2, and
at least one plasticizer PL.

The water-insoluble film-forming polymer P1 can be chosen from the group consisting of water-insoluble cellulose derivatives in particular ethylcellulose, cellulose acetate, cellulose acetate butyrate; ammonio (meth)acrylate copolymers, in particular of type A (e.g.: Eudragit RL) or of type B (e.g.: Eudragit RS); ethylene and vinyl acetate copolymers; and mixtures thereof.

The water-soluble polymer P2 can be chosen from the group consisting of polyvinylpyrrolidone (PVP); soluble cellulose derivatives such as hydroxypropyl-methylcellulose (HPMC), methylcellulose, hydroxyethyl cellulose, hydroxyethyl-methylcellulose, hydroxypropylcellulose, sodium carboxymethylcellulose; isomalt; maltodextrin; poloxamers; polyethylene glycol; polyvinyl alcohol; vinylpyrrolidone-vinyl acetate copolymer; xanthan gum; acacia gum; carragheenan gum; guar gum; carob gum; agar-agar; polydextrose; methylvinyl ether and maleic anhydride or maleic acid copolymers; and mixtures thereof, this polymer preferably being polyvinylpyrrolidone.

The plasticizer PL is chosen from the group consisting of glyceryl esters, phthalates, citrates, sebacates, in particular dibutyl sebacate, cetyl alcohol esters, castor oil, polyethylene glycol; and mixtures thereof;
More specifically, this coating can comprise:
50 to 90% insoluble film-forming polymer P1,
2 to 25%, preferably 5 to 15%, water-soluble polymer P2, and
2 to 20%, preferably 4 to 15% of a plasticizer PL.

More particularly, in this coating, P1 is chosen from the group consisting of ethylcellulose, cellulose acetate, cellulose acetate butyrate, ammonio (meth)acrylate copolymers, ethylene and vinyl acetate copolymers, P2 is preferably a polyvinylpyrrolidone and the plasticizer PL is preferably castor oil or dibutyl sebacate.

By way of example, such a coating can comprise 50 to 90% ethylcellulose, 2 to 25% polyvinylpyrrolidone and 2 to 20% castor oil.

The quantities of P1, P2 and PL preferably conform to the following characteristics: the fraction by mass as dry weight of P1 with respect to the total mass of the coating is comprised between 40 and 90%, the fraction by mass as dry weight P2/P1+P2 is comprised between 15 and 60% and the fraction by mass as dry weight PL/P1+PL is comprised between 1 and 30%.

According to another variant of the invention, the controlled-release coating comprises:
a polymer A chosen from the group consisting of cellulose derivatives: cellulose acetate phthalate, hydroxypropylmethylcellulose phthalate, cellulose acetate succinate, cellulose acetate trimellitate, hydroxypropylmethylcellulose acetate succinate; carboxymethylethylcellulose; (meth)acrylic acid copolymers (EUDRAGIT® S or L); polyvinyl acetate phthalate; and mixtures thereof, and
a compound B chosen from the group consisting of hydrogenated vegetable oils, triglycerides, and mixtures thereof. As triglycerides are modified natural products, it is understood that the triglycerides can contain a minority in particular of mono- and/or diglycerides,
the weight ratio B/A being comprised between 0.25 and 1.5, preferably between 0.5 and 1.

This coating allows a release of the active principle which is both delayed and controlled.

According to yet another variant, the controlled-release coating comprises a substance composed of at least:
10 to 75% by weight with respect to the total weight of said coating of at least one polymer which is insoluble in water,
25 to 90% by weight with respect to the total weight of said coating of at least one polymer bearing free carboxyl groups, and
0 to 25% by weight with respect to the total weight of said coating of at least one plasticizer,
said polymers being present in a weight ratio: [polymer(s) bearing free carboxyl groups/water-insoluble polymer(s)] at least equal to 0.25.

The water-insoluble polymer can be chosen from ethylcellulose, cellulose acetate butyrate, cellulose acetate, ammonio (meth)acrylate copolymers, in particular of type A or of type B, poly(meth)acrylic acid esters and mixtures thereof and the polymer bearing free carboxyl groups can be chosen from methacrylic acid and methyl methacrylate copolymer(s), methacrylic acid and ethyl acrylate copolymers, cellulose derivatives such as cellulose acetate phthalate, cellulose acetate succinate, cellulose acetate trimellilate, hydroxypropylmethylcellulose phthalate, hydroxypropylmethylcellulose acetate succinate, carboxymethylethylcellulose; shellac gum, polyvinyl acetate phthalate; and mixtures thereof.

Preferably, this coating is formed by at least a mixture of ethylcellulose, cellulose acetate butyrate or ammonio (meth) acrylate copolymer of type "A" or "B" with at least one methacrylic acid and ethyl acrylate copolymer or methacrylic acid and methyl methacrylate copolymer or a mixture thereof.

A controlled-release coating, whatever type is chosen, can moreover comprise additives currently used by a person skilled in the art such as for example a lubricant or a surfactant such as magnesium stearate or polyoxyethylenated hydrogenated castor oil.

According to a particular embodiment of the invention, it may be necessary to apply an additional layer between the active principle layer and the layer of controlled-release coating, acting to protect the active principle, in particular vis-à-vis oxygen or humidity of air, and/or one of the components of the coating layer. This additional layer can be applied at the rate of a few percent by mass by a technique known to a person skilled in the art, for example by the technique of spray coating in a fluidized bed and will principally consist of a film-forming polymer chosen from the polymers known to a person skilled in the art for their protective action, such as the hydroxypropyl methylcellulose or polyvinyl alcohol polymers available from Colorcon Limited (Dartford UK).

Film-Coating Ratio:
In the composition according to the invention, the coated microparticles are such that said coating film is sufficiently thick to provide a controlled permeability and industrial reproducibility, and sufficiently thin not to alter the apparent density significantly and allow the microparticles to float for several hours. Thus, in order to have both the desired apparent density and the desired release profile of the active principle, a person skilled in the art can adjust the film-coating ratio of the controlled-release coating; the "film-coating ratio Tp" being the fraction by mass of the layer of controlled-release coating with respect to the total mass of the coated microparticle, and being calculated as follows:

$$Tp = \frac{\text{weight of the controlled-release coating}}{\text{total weight of the coated microparticles}} \times 100$$

According to a particular embodiment of the invention, the film-coating ratio Tp of the coating layer allowing control of the active principle release is comprised between 5 and 50%, preferably between 10 and 40%, even more preferably between 15 and 30%.

Such a film-coating ratio is sufficient to provide the desired release profile of the active principle in an industrially reproducible manner, without however increasing the apparent density of the coated microparticles beyond 0.7 g/mL, preferably beyond 0.6 g/mL, and even more preferably beyond 0.5 g/mL, in order to ensure good floatability.

Thus, according to the choice of the coating and its composition, it is possible to adjust the release of the active principle while retaining its ability to float and therefore to better synchronize this release with the residence time in the stomach and the absorption kinetics of the active principle.

In view of the structure of the coated microparticles used in the pharmaceutical composition of the invention, it is possible on the one hand to regulate the flotation of the floating core by selecting the floating core by its apparent density and/or its floatability and/or its closed porosity, and on the other hand to modulate control of the release of the active principle by the nature of the controlled-release coating and the film-coating ratio, in order to be able to easily synchronize the residence time in the stomach and the duration of release so as to optimize the effectiveness of the active principle.

The pharmaceutical composition according to the present invention is presented in the form of sachets, suspensions, gelatin capsules, tablets or orodispersible tablets for oral administration. Apart from the microparticles described previously, it can comprise excipients known to a person skilled in the art, such as in particular compression agents, binders, disintegrants, lubricants, viscosifiers, fluidifiers, colorants, sweeteners, etc.

A subject of the present invention is also a controlled-release coated microparticle having an apparent density of less than or equal to 0.7 g/mL, comprising a core on the surface of which is deposited a layer containing at least one active principle, said layer being covered with a controlled-release coating, characterized in that said core is composed of cellulose acetate phthalate and has an apparent density of less than or equal to 0.6 g/mL.

A subject of the present invention is also a controlled-release coated microparticle comprising a floating core on the surface of which is deposited a layer containing at least one active principle, said layer being covered with a controlled-release coating, characterized in that said floating core is composed of cellulose acetate phthalate.

The microparticles according to the invention advantageously have a floatability F as measured according to the flotation test described hereafter in the TESTS section, greater than or equal to 50% after 1 hour, preferably greater than or equal to 50% after 4 hours, more preferably greater than or equal to 50% after 6 hours and even more preferably greater than or equal to 50% after 8 hours.

A subject of the present invention is also the use of a core composed of cellulose acetate phthalate to provide a microparticle comprising said core with a floatability F greater than or equal to 50% after at least 1 hour according to the flotation test as defined hereafter in the TESTS section.

The present invention also relates to a method of therapeutic treatment consisting essentially of administering the composition of the present invention by the oral route.

Preparation of the Pharmaceutical Compositions

The process for the preparation of the compositions of the invention comprises the following successive stages:
a) selection of a floating core,
b) optionally, selective sieving
c) applying the active principle, optionally in the presence of a binder, to the surface of the floating core,
d) optionally applying a protective film,
e) applying a controlled-release coating.

The process can optionally comprise an additional stage of mixing with excipients, optionally followed by a compression stage.

Stage a) of selection of the floating cores is carried out according to the properties as they are mentioned above, namely their apparent density, size, mechanical strength and/or their closed porosity.

Stages c), d) and e) are carried out by standard particle techniques used for coating particles, in particular by spray coating in a fluidized bed.

This preparation process can be carried out easily on any type of installation for coating microparticles.

The invention is described in greater detail using the examples and figures hereafter which are non-limitative and given by way of illustration only.

TESTS

Figure 1:
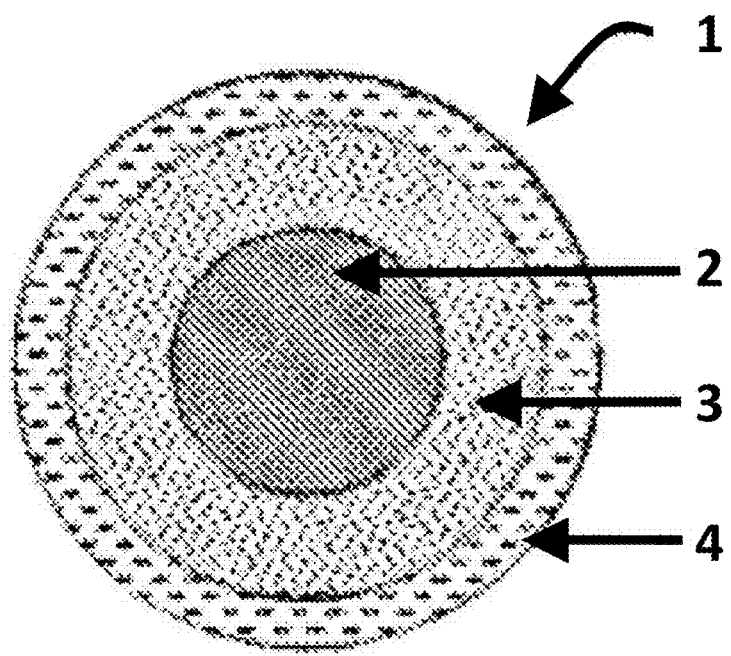
FIG. 1 is a diagrammatic representation in cross-section of a coated microparticle used in the pharmaceutical compositions of the invention where 1 is the coated microparticle, 2 is the floating core, 3 is the layer comprising the active principle and 4 is the controlled-release coating.

Measurement of the Apparent Density after Settling ($\rho_a$)

The measurement method is based on the test of the apparent volume described in the European Pharmacopoeia, edition 6.4, chapter 02.09.34. The apparatus is constituted by a settling device which can carry out 250 falls per minute from a height of 3 mm and a 250 mL measuring cylinder. 100.0 g of powder is introduced into the dry cylinder. If the corresponding volume is greater than 250 cm³, then a mass of 50 g only is introduced. A reading of the volume of the powder is performed after 1250 falls have been carried out. The ratio between the mass introduced and the volume read corresponds to the settled apparent density, expressed in g/mL.

Measurement of the Effective Particle Density ($\rho_p$)

The device used is a liquid pycnometer. The liquid used is a solution of hydrochloric acid of normality 0.1 N containing 0.5% (by weight) of Tween 20 surfactant at ambient temperature. The pycnometer filled with the liquid ($M_1$) is accurately weighed. The powder sample taken for measurement ($M_2$) is weighed. The pycnometer containing the powder sample to be measured and made up with the liquid ($M_3$) is accurately weighed. The effective particle density is calculated as follows, $\rho_e$ being the density of the liquid.

$$\text{Effective particle density} = \frac{M_2 \rho_e}{M_1 + M_2 - M_3}$$

Measurement of Flotation F

The performances of the pharmaceutical compositions or their constituents (coated microparticles, floating cores) are measured using a flotation test which makes it possible to assess both their ability to float on the surface of the aqueous medium in which they are immersed, but also their ability to return to the surface after having been sent to the bottom of the container by stirring the medium. Such a test consists of pouring 300 to 500 mg of product to be tested into 500 mL of a solution of hydrochloric acid of normality 0.1 N containing 0.5% by weight of Tween 80 surfactant, kept at 37° C. for the duration of the test. A dissolution device is used such as a paddle dissolutest described in the European Pharmacopoeia. The medium is vigorously stirred using a spatula in order to allow the total immersion of the product. Then the stirring is adjusted to 50 rpm during the observation. After 1 hour, 4 hours, 6 hours and/or 8 hours, the floating particles are removed and weighed (a mass Mf is obtained) and the particles which have sunk are collected and weighed (a mass Mc is obtained), the following value is calculated $$F = \frac{Mf}{Mc + Mf} \times 100$$

The pharmaceutical compositions of the invention are declared "floating systems" if F is greater than or equal to 50% after 1 hour, preferably after 4 hours, even more preferably after 6 hours and even more preferably after 8 hours.

Measurement of the Equivalent Volume Diameter D[4;3]

The mean diameter is determined by laser diffraction or sieve analysis according to the scale of size to be characterized.

Up to a size of 1000 µm, the particle size distribution is measured by laser diffraction using a Mastersizer 2000 device equipped with a dried powder sampler. The equivalent volume mean diameter or D(4;3) is calculated from the grain size distribution measured over a wide range, according to the following formula:

$$D(4;3) = \Sigma(d^4)/\Sigma(d^3)$$

For a size greater than 1000 µm, the analytical sieving method is used. The choice of sieve is easily made by a person skilled in the art by way of reference to the European Pharmacopoeia, edition 6.4, chapter 02.09.38.

Measurement of Friability

The friability test consists of measuring the diameter D(4;3) using a dry mode laser granulometer at a pressure of 0.1 bar (i.e. $D_{0.1}$), then at a pressure of 2 bars (i.e. $D_2$), the friability being equal to:

$$\frac{D_{0.1} - D_2}{D_{0.1}} \times 100$$

EXAMPLES

In the examples, the following abbreviations are used:
CAP or Cellacefate: cellulose acetate phthalate, marketed by Eastman Chemicals Company (UK) under the trade mark Eastman™ C-A-P Cellulose Ester NF
Plasdone K29/32: polyvinylpyrrolidone marketed by ISP
Ethocel 7 premium: ethylcellulose marketed by Dow Chemicals
TEC: triethyl citrate marketed by Morflex
Eudragit L100-55: methacrylic acid/methyl methacrylate copolymer marketed by Evonik
Lubritab: hydrogenated vegetable oil/hydrogenated oil, marketed by JRS Pharma Example 1

Characterization of CAP "Cellacefate Pellets"

Figure 2:
FIG. 2 is a binocular microscope photograph of cellulose acetate phthalate granules "Cellacefate Pellets" characterized in Example 1 of the invention (magnification 0.6×1.6).

The "Cellacefate pellets" are observed with a binocular microscope and they are photographed (FIG. 2). Their shape is ovoid with a smooth surface.

The apparent density $\rho_a$ of the "Cellacefate pellets" is determined according to the method described above and is equal to 0.324 g/cm³

The effective particle density $\rho_p$ measured in water using a pycnometer is equal to 0.514 g/cm³.

The true density $\rho_v$ measured using a helium pycnometer is equal to 1.3932 g/cm³.

The closed porosity is 0.631=1-($\rho_p/\rho_v$)

The flotation of the "Cellacefate pellets" is assessed according to the test described above. All of the particles remain on the surface of the aqueous medium after 24 h.

It was not possible to determine the friability of these pellets as the size exceeds the upper limit of the range of use of the machine (>1000 µm). It is estimated that it is similar to that of "Cellacefate Powder".

Example 2

Characterization of CAP "Cellacefate Powder"

100 g of CAP "Cellacefate Powder" is sieved through a nest of sieves with aperture sizes comprised between 1000 et 50 µm. The materials remaining on each sieve are measured and the accumulated oversize fractions are calculated (table). The D50 by sieving is equal to approximately 550 µm.

| Sieve aperture size (µm) | % accumulated oversize |
| --- | --- |
| 1000 | 11 |
| 800 | 23 |
| 630 | 42 |
| 500 | 55 |
| 400 | 63 |
| 300 | 76 |
| 200 | 87 |
| 50 | 100 |
| 0 | 100 |

955 g of "Cellacefate Powder" is manually sieved in sieves equipped with a sieve cloth of 50 µm, 500 µm and 1000 µm. 499 g comprised between 500 and 1000 µm is isolated.

Figure 3:
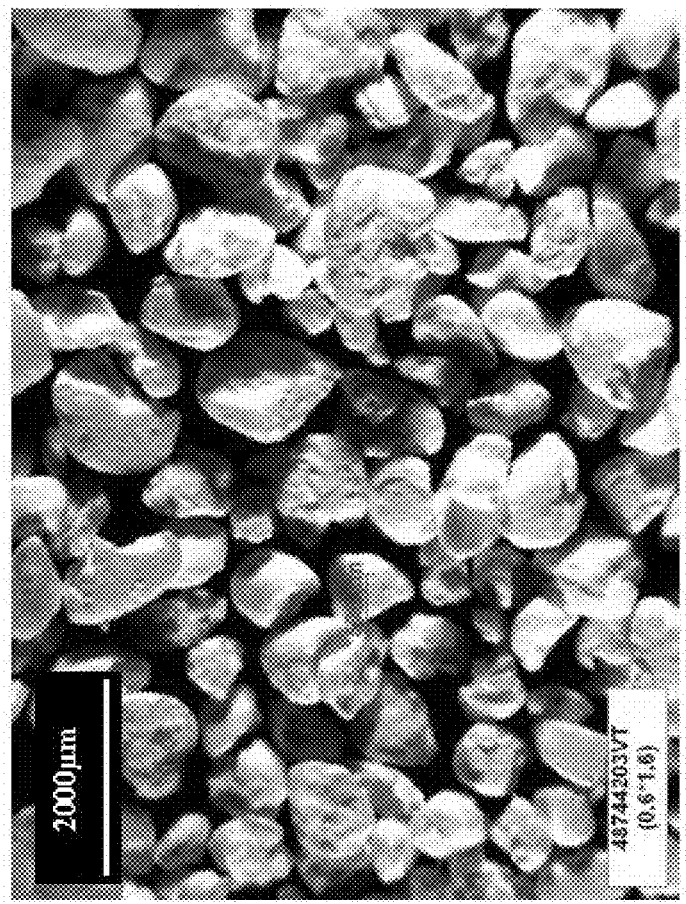
FIG. 3 is a binocular microscope photograph of the 500-1000 μm fraction obtained by sieving the cellulose acetate phthalate "Cellacefate Powder" of Example 2 of the invention (magnification 0.6×1.6).

This 500-1000 µm fraction of "Cellacefate Powder" is observed with a binocular microscope (magnification 0.6× 1.6) and they are photographed (FIG. 3). Their shape is ovoid with a smooth surface.

The volume mean diameter at 0.1 bar and 2 bar and the friability of the "Cellacefate Powder" 500-1000 µm are obtained by laser granulometry with the Malvern Scirocco 2000 dry-mode module, in accordance with the test described above.

| Pressure (in bar) | Diameter [4; 3] (in µm) |
| --- | --- |
| 0.1 | 973 |
| 2 | 948 |
| Friability: | 3% |

The apparent density of the "Cellacefate Powder" 500-1000 µm is determined according to the method described above and is equal to 0.290 g/cm$^3$ The flotation of the "Cellacefate Powder" 500-1000 µm was assessed using the above-described flotation test: 50% of the particles remain on the surface of the aqueous medium after 1 h.

Example 3

Production of Floating Granules of Carvedilol Phosphate

Floating granules of carvedilol phosphate are prepared as follows: 360 mL of demineralized water, then 540 mL of ethanol are introduced into a stainless steel beaker. 60 g of Plasdone K29/32 is introduced into this mixture and stirred for 15 minutes at 600 rpm (revolutions per minute). Then, 240 g of carvedilol phosphate is added and the mixture is homogenized. 300 g of CAP is introduced into a fluidized bed reactor of the GLATT GPCG1-1 type in the form of pellets marketed by Eastman Chemicals under the trade mark "Cellacefate pellets" and the whole of the previously-obtained solution is sprayed.

531 g of floating carvedilol phosphate granules is obtained.

Example 4

Production of Floating Controlled-Release Carvedilol Phosphate Particles 2.12 g of castor oil and 5.29 g of TEC are introduced into a stainless steel beaker, then 426.18 g of ethanol is introduced and stirred for 15 minutes at 600 rpm. Then 9.53 g of Plasdone K29/32, 36 g of Ethocel 7 premium are added under vigorous stirring until dissolved. Then 182.65 g of demineralized water is added.

300 g of floating granules of carvedilol phosphate obtained in Example 3 is introduced into a fluidized bed reactor of the Glatt GPCG1-1 type and the whole of the prepared solution is sprayed in order to obtain a film-coating ratio of 15% as defined in the description. 328 g of controlled-release floating particles is obtained.

These particles are represented diagrammatically in FIG. 1 in which the particle 1 comprises a substrate 2 on which is deposited a layer 3 of active principle, which is itself coated with a controlled-release layer 4. Although described in connection with Example 1, this figure represents generally the particles used in the compositions of the invention.

Figure 4:
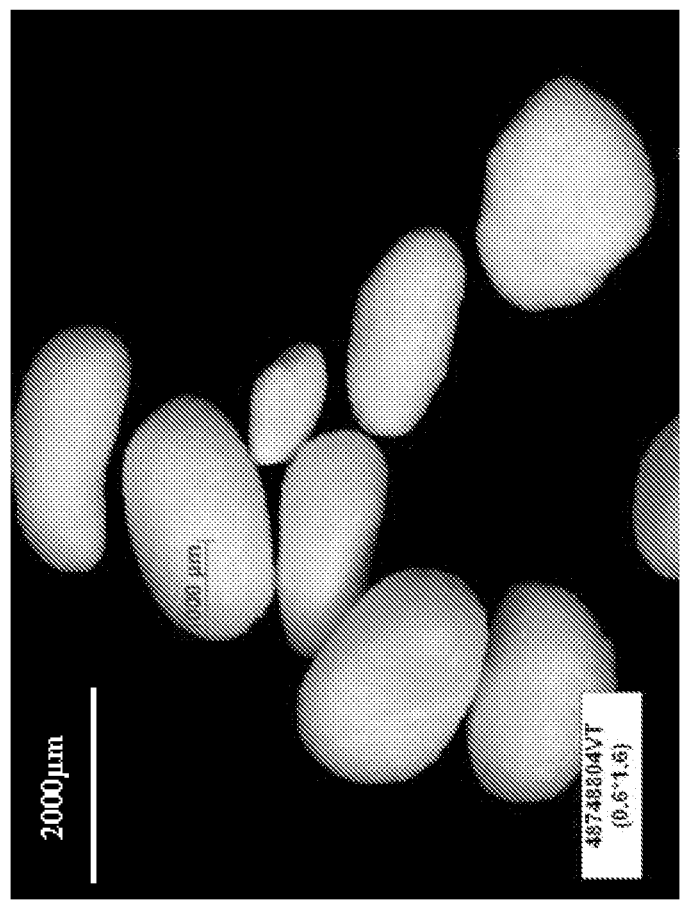
FIG. 4 is a binocular microscope photograph of cellulose acetate phthalate granules coated with a film-coating ratio of 20%, prepared according to Example 4 of the invention.

These particles are photographed under a binocular microscope (FIG. 4). The film-coating obtained is uniform over the entire surface of the particles.

The apparent density of these particles is determined according to the method described above and is equal to 0.429 g/cm$^3$.

These particles are tested as regards flotation according to the test described above. The results are given in the table below: After 6 h, 75% of the particles are still floating on the surface of the aqueous medium.

| time (hours) | Fraction of particles on the surface of the aqueous medium |
| --- | --- |
| 0 | 100% |
| 1 | 100% |
| 2 | 90% |
| 3 | 75% |
| 4 | 75% |
| 6 | 75% |

Measurement of the Dissolution of Carvedilol Phosphate

Figure 5:
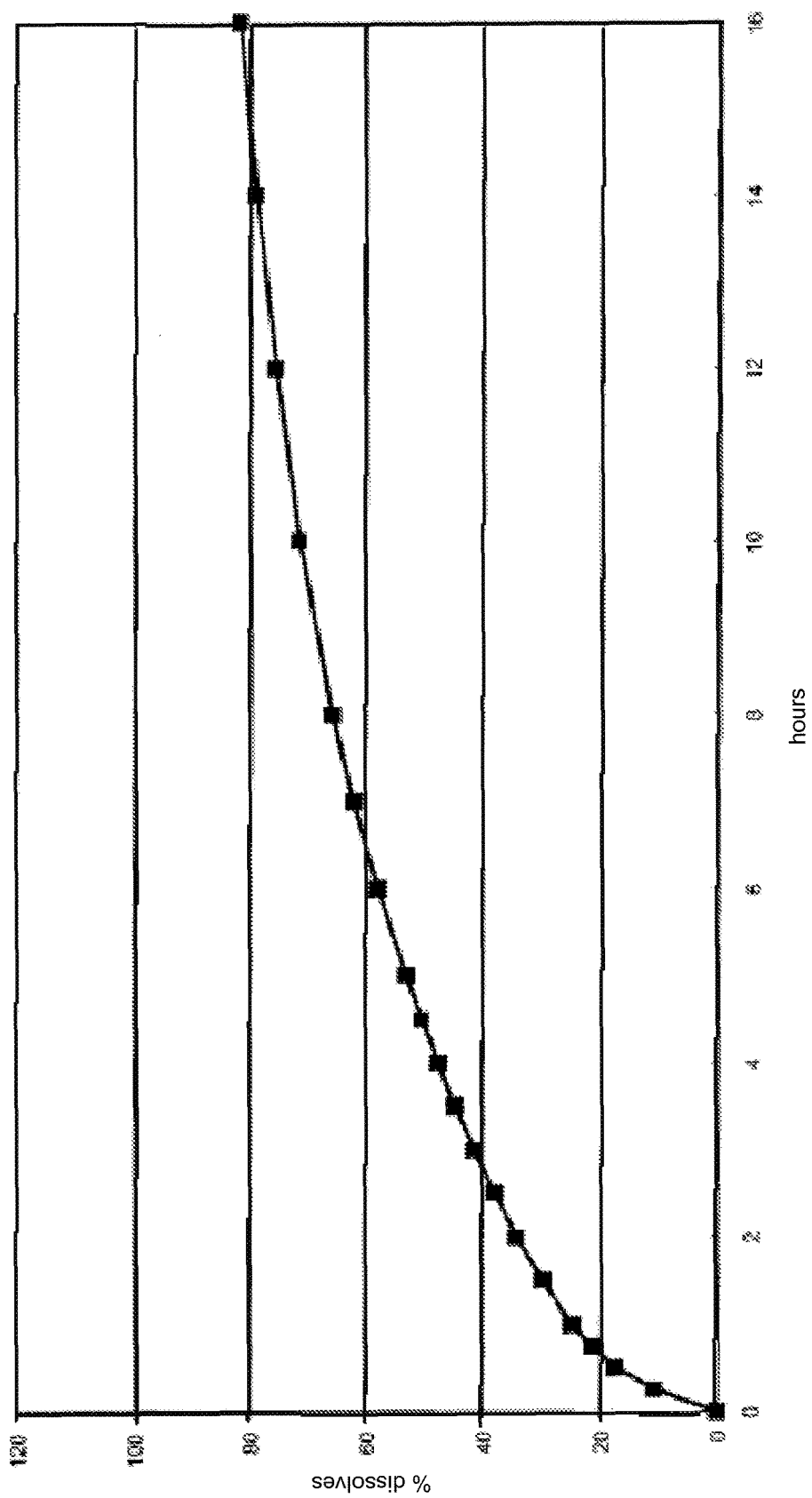
FIG. 5 is a graph representing the percentage of carvedilol phosphate dissolved in 0.1 N HCl as a function of time for the floating particles of Example 4.

Dissolution of the carvedilol phosphate in the 0.1 N HCl medium is monitored by measuring the UV absorbance at the wavelength of 285 nm in cells of 0.5 cm by comparison with a previously-established testing graph. A quantity of particles corresponding to approximately 80 mg of carvedilol phosphate is introduced into 900 mL of medium per vessel of the dissolution device, equipped with stirring paddles rotating at 100 rpm (dissolution device II of the European Pharmacopoeia) and kept at 37° C. An automatic sampling is carried out at predetermined intervals and recycled after the absorbance has been read. The curve representing the fraction of carvedilol dissolved as a function of time is shown in FIG. 5.

Example 5

Production of Floating Granules of Carvedilol Phosphate

The procedure is the same as in Example 3 but replacing the granules of CAP "Cellacefate pellets" by the fraction comprised between 500 and 1000 µm obtained by sieving "Cellacefate Powder".

507 g of floating carvedilol phosphate granules is obtained at a coating ratio of 50%.

Example 6

Production of Floating Microparticles of Controlled-Release Carvedilol Phosphate The procedure is the same as in Example 4 but using the floating carvedilol phosphate granules obtained in Example 5 and spraying a quantity of film-coating solution corresponding to a final film-coating ratio of 20%.

Figure 6:
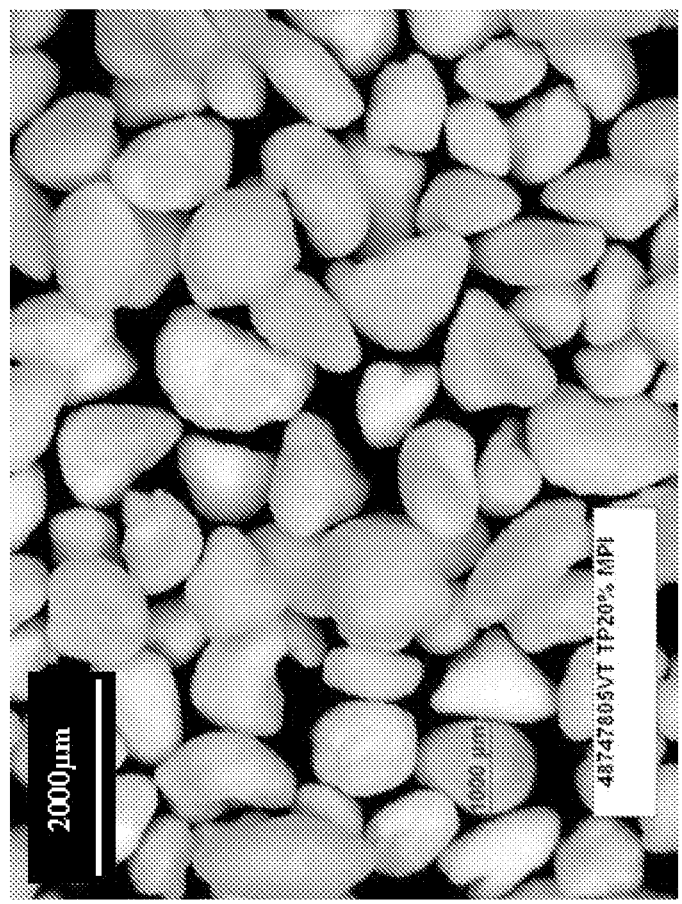
FIG. 6 is a binocular microscope photograph of cellulose acetate phthalate granules coated with a film-coating ratio of 20%, prepared according to Example 6 of the invention.

The film-coating is uniform over the whole of the surface of the microparticles. The coated microparticles thus obtained were observed with a binocular microscope. The corresponding photograph is given in FIG. 6.

The apparent density of these particles, determined according to the method described above, is equal to 0.457 g/cm³

The volume mean diameter is approximately 1027 µm.

These particles are tested as regards flotation according to the test described above. The results obtained are given in the table below.

| time (hours) | Fraction of particles on the surface of the aqueous medium |
| --- | --- |
| 0 | 100% |
| 1 | 90% |
| 2 | 75% |
| 3 | 75% |
| 4 | 67% |
| 5 | 50% |
| 6 | 25% |

Figure 7:
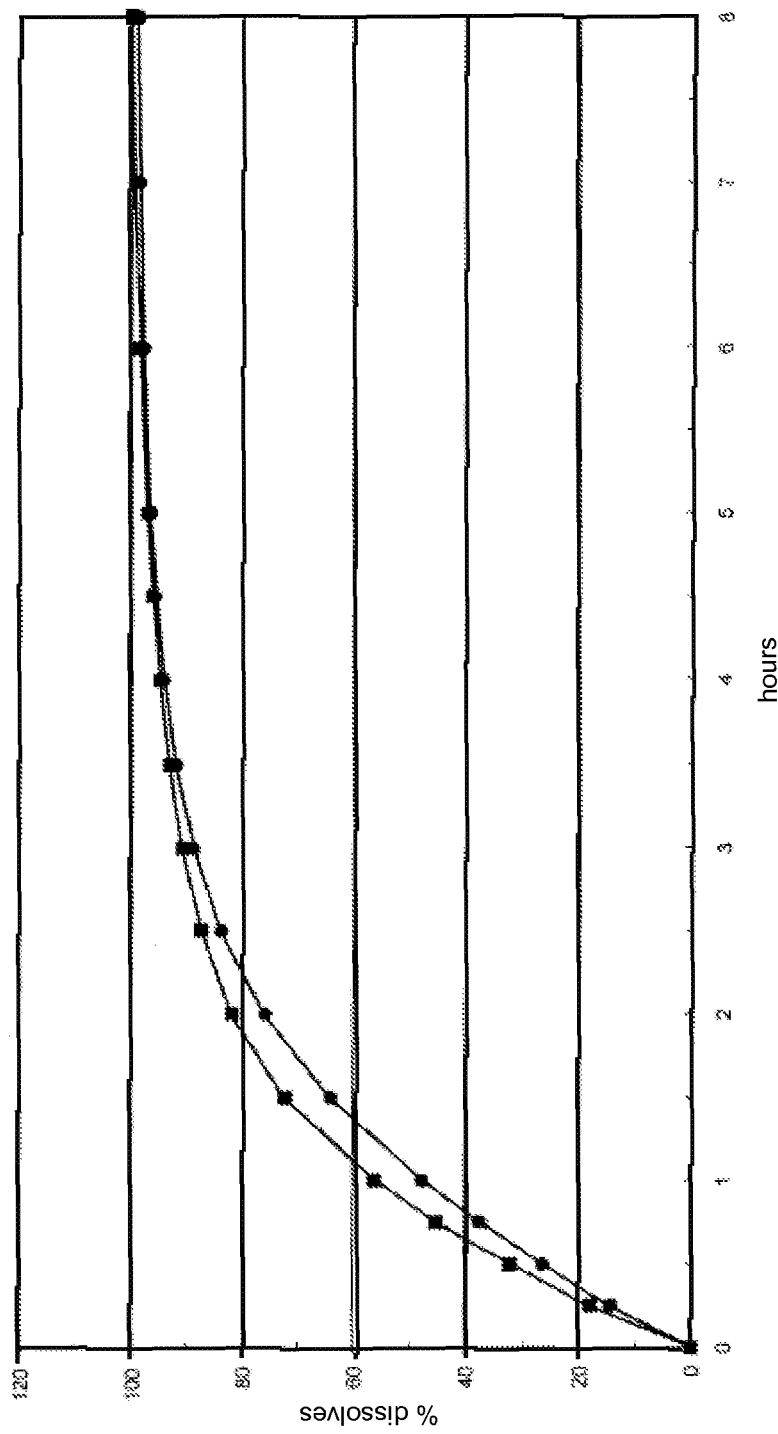
FIG. 7 is a graph representing the percentage of carvedilol phosphate dissolved in 0.1 N HCl as a function of time for the floating particles prepared in Example 6 at a film-coating ratio of 20% for the curve with black circles and a film-coating ratio of 15% for the curve with black squares.

Dissolution of the carvedilol phosphate in the 0.1 N HCl medium is monitored under the same conditions as for Example 4. The curve representing the dissolved fraction of carvedilol as a function of time is shown on the curve with black circles in FIG. 7.

The same procedure as the above is used, but spraying a quantity of film-coating solution corresponding to a final film-coating ratio of 15%. Dissolution of the carvedilol phosphate is monitored as above and the results are shown on the curve with black squares in FIG. 7.

Example 7

Production of Floating Granules of Ibuprofen

Floating granules of ibuprofen are prepared as follows. 175 g of acetone, 11.25 g of Klucel EF are introduced into a stainless steel beaker under stirring, then 63.75 g of ibuprofen is added and the mixture is homogenized. 300 g of "Cellacefate pellets" is introduced into a fluidized bed reactor of the Glatt GPCG1-1 type and the whole of the previously-obtained solution is sprayed. 360 g of floating granules of ibuprofen is obtained.

These granules are tested as regards flotation according to the test described previously.

After 20 hours, all of the granules float on the surface of the aqueous medium.

Example 8

Production of Floating Microparticles of Controlled-Release Ibuprofen 6 g of castor oil and 1.5 g of Cremophor RH40 are introduced into 517.5 g of acetone and 345 g of isopropanol in a suitable stainless steel beaker under stirring. Then 7.5 g of Plasdone K29/32 is added. After dissolution, 60 g of Ethocel 20 is added and left under vigorous stirring until dissolved.

Granules obtained in Example 7 above are introduced into a fluidized bed reactor of the Glatt GPCG1-1 type and the previously-prepared solution is sprayed in order to obtain a film-coating ratio of 20%. Then, controlled-release microparticles of ibuprofen are obtained.

The apparent density measured is equal to 0.363 g/cm³.

These particles are tested as regards flotation according to the test described above: they all remain on the surface of the medium for at least 20 h.

Figure 8:
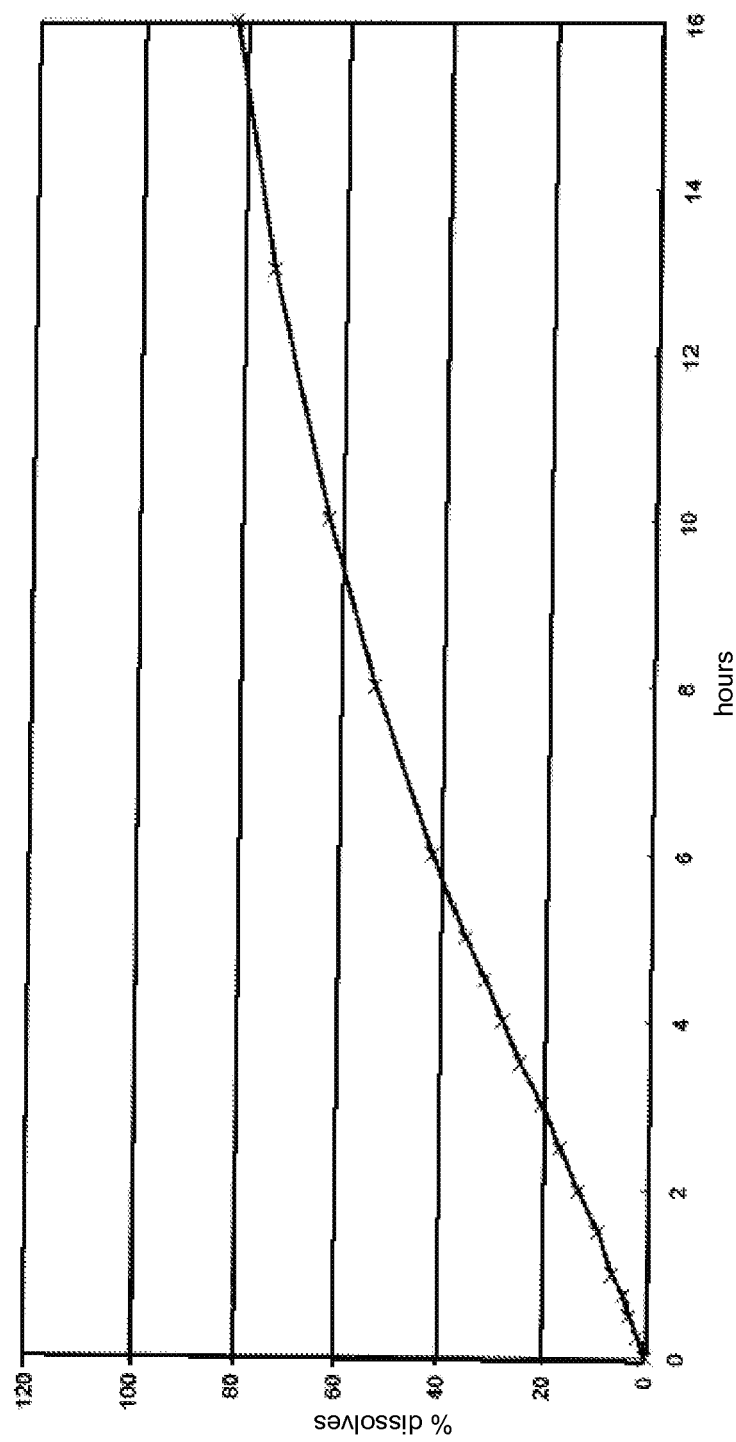
FIG. 8 is a graph representing the percentage of ibuprofen dissolved in 0.1 N HCl as a function of time for the floating particles prepared in Example 8 (curve with crosses).

Dissolution of ibuprofen in the 0.1 N HCl medium is monitored under the same conditions as for Example 4. The curve representing the dissolved fraction of ibuprofen as a function of time is shown in FIG. 8.

Example 9

Production of Floating Granules of Metformin HCl

Floating granules of metformin HCl are prepared as follows. 500.0 g of metformin HCl is dissolved in 690.5 g of water in a stainless steel beaker under stirring. 500 g of "Cellacefate pellets" is introduced into a fluidized bed reactor of the Glatt GPCG1-1 type and the whole of the previously-obtained solution is sprayed. 960 g of metformin HCl granules is obtained.

Example 10

Production of Controlled-Release Floating Microparticles of Metformin HCl 30.0 g of Eudragit L100-55; 15.0 g of Eudragit S100 and 30.0 g of Lubritab are dissolved in 675.0 g of isopropanol in a suitable stainless steel beaker under stirring.

425.0 g of the granules obtained in Example 9 above is introduced into a fluidized bed reactor of the Glatt GPCG1-1 type and the previously-prepared solution is sprayed. Controlled-release metformin HCl microparticles are then obtained at a coating ratio of 15%.

The same solution is subsequently sprayed onto a fraction of the microparticles obtained in order to obtain a final coating ratio of 28%.

Figure 9:
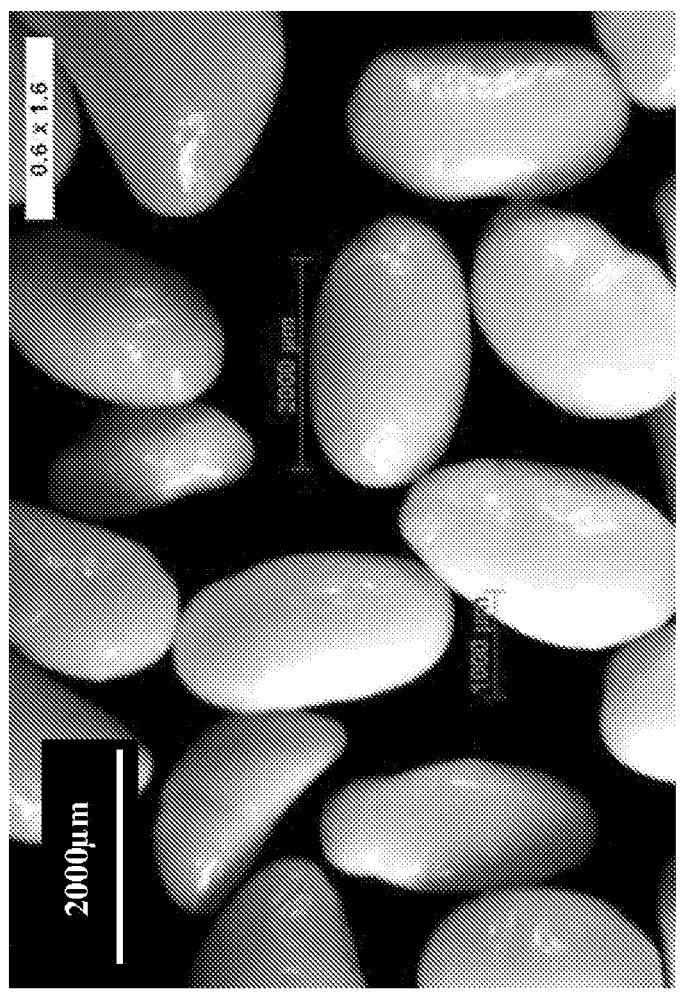
FIG. 9 is a binocular microscope photograph of cellulose acetate phthalate granules coated with a film-coating ratio of 28%, prepared according to Example 10 of the invention.

The coated microparticles thus obtained were observed with a binocular microscope. The corresponding photograph is given in FIG. 9.

The apparent density measured is equal to 0.52 g/cm³.

These two batches of particles are tested as regards flotation according to the test described above: 95% of the particles remain on the surface of the medium for 8 h and 70% are still present on the surface after 24 h.

Dissolution of the metformin HCl in a 0.1 N HCl+0.5% Tween 20 medium is monitored by measuring the UV absorbance at the wavelength of 232 nm in cells of 0.1 cm by comparison with a previously-established testing graph. A quantity of particles is introduced into 900 mL of medium per vessel of the dissolution device, equipped with stilling paddles rotating at 100 rpm (dissolution device II of the European Pharmacopoeia) and kept at 37° C. An automatic sampling is carried out at predetermined intervals and recycled after the absorbance has been read.

Figure 10:
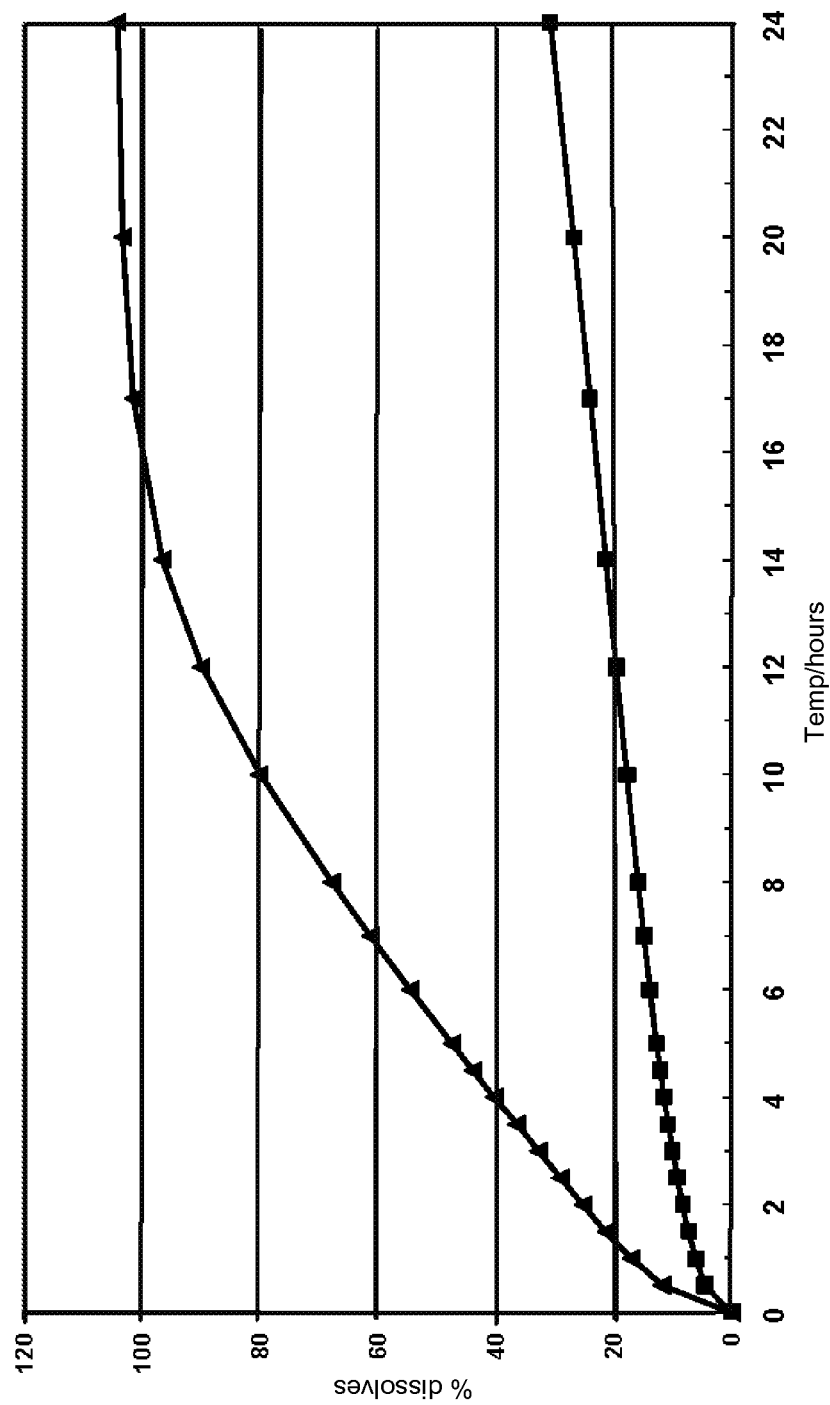
FIG. 10 is a graph representing the percentage of metformin HCl dissolved in 0.1 N HCl+0.5% Tween 20 as a function of time for the floating particles prepared in Example 10 at a film-coating ratio of 15% for the curve with black triangles and at a film-coating ratio of 28% for the curve with black squares.

The curves representing the accumulated fraction of metformin HCl dissolved as a function of time are shown in FIG. 10 (black triangles for the coating ratio of 15%; black squares for the coating ratio of 28%).

The invention claimed is:

1. A pharmaceutical composition comprising a plurality of controlled-release coated microparticles each comprising a floating core, on the surface of which is deposited a layer containing at least one active principle, without any intermediate layer, said layer containing at least one active principle being covered with a controlled-release coating,
   wherein said floating core has a closed porosity greater than or equal to 0.2,
   wherein said floating core comprises cellulose acetate phthalate and does not comprise any active principle and has an apparent density of less than or equal to 0.6 g/mL and
   wherein said coated microparticles have an apparent density of less than or equal to 0.7g/mL.

2. The pharmaceutical composition of claim 1, wherein the floating core is porous and has a floatability F, as measured according to a flotation test, greater than or equal to 50% after 1 hour,
   wherein said flotation test comprises:
   pouring 300 to 500 mg of floating cores to be tested into 500 mL of a solution of hydrochloric acid of normality 0.1 N containing 0.5% by weight of Tween 80 surfactant, kept at 37° C. for the duration of the test, using a paddle_dissolution device,
   vigorously stirring the medium using a spatula to allow the total immersion of the floating cores,
   applying a stirring to the medium by adjusting the rotation speed of the paddle of the dissolution device to 50 rpm,
   removing and weighing the floating particles after 1 hour (a mass Mf is obtained),
   collecting and weighing the particles which have sunk (a mass Mc is obtained),
   calculating:

$$F = \frac{Mf}{Mc + Mf} \times 100.$$

3. The pharmaceutical composition of claim 1, wherein the floating core has a mechanical strength, as measured by a friability test, of less than 30%,
   wherein said friability test consists of:
   measuring an equivalent volume mean diameter D(4;3) of the floating cores using a dry mode laser granulometer at a pressure of 0.1 bar (a diameter $D_{0.1}$ is obtained), then at a pressure of 2 bars (a diameter $D_2$ is obtained), $$\text{calculating the friability} = \frac{D_{0.1} - D_2}{D_{0.1}} \times 100.$$

4. The pharmaceutical composition of claim 1, wherein an equivalent volume mean diameter of the floating core is within one of the following ranges: 50 to 500 µm, 500 to 1000 µm, or 1000 to 4000 µm.

5. The pharmaceutical composition of claim 1, wherein the floating core is a cellulose acetate phthalate granule.

6. The pharmaceutical composition of claim 5, wherein the cellulose acetate phthalate contained in the granule comprises: 30 to 36% of phthalyl groups, 21.5 to 26% acetyl groups, a maximum of 5.0 weight % of moisture and a maximum of 3.0 weight % of free acid as phthalic acid.

7. The pharmaceutical composition of claim 1, wherein the controlled-release coating comprises:
   50 to 90% water-insoluble polymer P1,
   2 to 25% water-soluble polymer P2, and
   2 to 20% plasticizer PL.

8. The pharmaceutical composition of claim 7, wherein:
   the water-insoluble film-forming polymer P1 is chosen from the group consisting of water-insoluble cellulose derivatives,
   the water-soluble polymer P2 is chosen from group consisting of polyvinylpyrrolidone (PVP); soluble cellulose derivatives; isomalt; maltodextrin; poloxamers; polyethylene glycol; polyvinyl alcohol; vinylpyrrolidone-vinyl acetate copolymer; xanthan gum; acacia gum; carragheenan gum; guar gum; carob gum; agar-agar; polydextrose; methylvinyl ether and maleic anhydride or maleic acid copolymers; and mixtures thereof; and
   the plasticizer PL is chosen from the group consisting of glyceryl esters, phthalates, citrates, sebacates, cetyl alcohol esters, castor oil, polyethylene glycol; and mixtures thereof.

9. The pharmaceutical composition of claim 7, wherein the quantities of P1, P2 and PL have the following characteristics: the fraction by mass as dry weight of P1 with respect to the total mass of the coating is between 40 and 90%, the fraction by mass as dry weight P2/(P1+P2) is between 15 and 60% and the fraction by mass as dry weight PL/(P1+PL) is between 1 and 30%.

10. The pharmaceutical composition of claim 1, wherein the controlled-release coating comprises:
    a polymer A chosen from the group consisting of cellulose derivatives, and
    a compound B chosen from the group consisting of hydrogenated vegetable oils, triglycerides, and mixtures thereof,
    the weight ratio B/A is between 0.25 and 1.5.

11. The pharmaceutical composition of claim 1, wherein the controlled-release coating comprises:
    10 to 75% by weight with respect to the total weight of said coating of at least one water-insoluble polymer;
    25 to 90% by weight with respect to the total weight of said coating of at least one polymer bearing free carboxyl groups; and
    0 to 25% by weight with respect to the total weight of said coating of at least one plasticizer,
    said polymers being present in a weight ratio [polymer(s) bearing free carboxyl groups / water-insoluble polymer(s)] at least equal to 0.25.

12. The pharmaceutical composition of claim 10, wherein the polymer A is chosen from the group consisting of cellulose acetate phthalate, hydroxypropyl methylcellulose phthalate, cellulose acetate succinate, cellulose acetate trimellitate, hydroxypropyl methylcellulose acetate succinate; carboxymethyl ethylcellulose; (meth)acrylic acid copolymers; polyvinyl acetate phthalate; and mixtures thereof, and and wherein the weight ratio B/A is between 0.5 and 1.

13. The pharmaceutical composition of claim 11,
wherein the at least one water-insoluble polymer is chosen from ethylcellulose, cellulose acetate butyrate, cellulose acetate, ammonio (meth)acrylate copolymers, poly(meth)acrylic acid esters, and mixtures thereof; and
wherein the at least one polymer bearing free carboxyl groups is chosen from methacrylic acid and methyl methacrylate copolymer(s), methacrylic acid and ethyl acrylate copolymer(s), cellulose acetate phthalate, cellulose acetate succinate, cellulose acetate trimellilate, hydroxypropyl methylcellulose phthalate, hydroxypropyl methylcellulose acetate succinate; carboxymethyl ethylcellulose; shellac gum; polyvinyl acetate phthalate; and mixtures thereof.

14. The pharmaceutical composition of claim 8, wherein:
the water-insoluble film-forming polymer P1 is chosen from the group consisting of ethylcellulose, cellulose acetate, cellulose acetate butyrate; ammonio (meth)acrylate copolymers; ethylene and vinyl acetate copolymers; and mixtures thereof,
the water-soluble polymer P2 is chosen from group consisting of hydroxypropyl methylcellulose (HPMC), methylcellulose, hydroxyethylcellulose, hydroxyethylmethylcellulose, hydroxypropylcellulose, sodium carboxymethylcellulose; and mixtures thereof.

* * * * *